(12) United States Patent
Chen et al.

(10) Patent No.: US 10,905,222 B2
(45) Date of Patent: Feb. 2, 2021

(54) PERSONALIZATION SKIN CARE PRODUCT SYSTEM, METHOD AND COMPUTER PROGRAM PRODUCT

(71) Applicant: VesCir Ltd., Taipei (TW)

(72) Inventors: Wei-Yu Chen, New Taipei (TW); Chia-Jung Tsai, New Taipei (TW)

(73) Assignee: VESCIR LTD., Taipei (TW)

( * ) Notice: Subject to any disclaimer, the term of this patent is extended or adjusted under 35 U.S.C. 154(b) by 213 days.

(21) Appl. No.: 16/174,334

(22) Filed: Oct. 30, 2018

(65) Prior Publication Data

US 2019/0142138 A1    May 16, 2019

Related U.S. Application Data

(60) Provisional application No. 62/584,974, filed on Nov. 13, 2017.

(51) Int. Cl.

| | | |
|---|---|---|
| *A45D 34/00* | (2006.01) | |
| *A45D 44/00* | (2006.01) | |
| *G09B 5/02* | (2006.01) | |
| *G09B 5/04* | (2006.01) | |
| *A61Q 19/00* | (2006.01) | |
| *A61K 8/73* | (2006.01) | |
| *A61K 8/98* | (2006.01) | |
| *A61K 8/31* | (2006.01) | |
| *A61K 8/9789* | (2017.01) | |

(Continued)

(52) U.S. Cl.
CPC ............. *A45D 44/00* (2013.01); *A45D 34/00* (2013.01); *A45D 40/24* (2013.01); *A45D 44/005* (2013.01); *A61K 8/31* (2013.01); *A61K 8/345* (2013.01); *A61K 8/44* (2013.01); *A61K 8/678* (2013.01); *A61K 8/735* (2013.01); *A61K 8/9706* (2017.08); *A61K 8/9789* (2017.08); *A61K 8/9794* (2017.08); *A61K 8/987* (2013.01); *A61K 8/988* (2013.01); *A61Q 19/00* (2013.01); *G09B 5/02* (2013.01); *G09B 5/04* (2013.01); *G09B 5/06* (2013.01); *G09B 19/0076* (2013.01); *A45D 2044/007* (2013.01); *A45D 2200/054* (2013.01); *A45D 2200/058* (2013.01)

(58) Field of Classification Search
CPC .. B01F 13/06; B01F 13/1063; B01F 13/1055; B01F 2215/0031; G07F 13/06; A45D 2004/007
USPC ........................................................ 700/233
See application file for complete search history.

(56) References Cited

U.S. PATENT DOCUMENTS

| | | | |
|---|---|---|---|
| 2010/0185322 A1* | 7/2010 | Bylsma ............... | B01F 13/1063 700/239 |
| 2013/0037043 A1* | 2/2013 | Samain ................. | G16H 40/63 132/200 |

(Continued)

*Primary Examiner* — Timothy R Waggoner
(74) *Attorney, Agent, or Firm* — Bacon & Thomas, PLLC

(57) ABSTRACT

A personalization skin care product system includes a measuring device and a processor. The measuring device measures a user's skin information; the processor executing a computer program product provides a personalization suggestion message according to the user's skin information; wherein, the personalization suggestion message corresponds to a user controllable interface of an adjustable skin care product device, wherein the adjustable skin care product device provides a personalization skin care product with different volume proportion of the ingredients according to the different instructions from the user controllable interface.

18 Claims, 12 Drawing Sheets

(51) Int. Cl.
*A61K 8/9794* (2017.01)
*A61K 8/9706* (2017.01)
*A61K 8/44* (2006.01)
*A61K 8/34* (2006.01)
*A61K 8/67* (2006.01)
*G09B 5/06* (2006.01)
*G09B 19/00* (2006.01)
*A45D 40/24* (2006.01)

(56) References Cited

U.S. PATENT DOCUMENTS

2014/0081463 A1* 3/2014 Igarashi .............. B01F 13/1063
　　　　　　　　　　　　　　　　　　　　　　　700/265
2016/0331308 A1* 11/2016 Zhou ...................... A61B 5/002

* cited by examiner

US 10,905,222 B2

PERSONALIZATION SKIN CARE PRODUCT SYSTEM, METHOD AND COMPUTER PROGRAM PRODUCT

BACKGROUND OF THE INVENTION

1. Field of the Invention

The present invention relates to a skin care product system, method and computer program product and, more particularly, to a personalization skin care product system, method and computer program product.

2. Description of Related Art

Human skin condition varies according to the changes in environmental factors (e.g. temperature, humidity, etc.) and daily physical conditions. To improve the skin condition, the skin care products that each one actually needs will also be different.

Most of the skin care products in the market are single-functioned, e.g. only for summer, winter, oil skin, dry skin, etc., and the formula of those skin care products are fixed, which cannot be adjusted to meet individuals' needs.

Besides, although a user may have multiple skin care products with different functions, the user still doesn't understand how to use those skin care products, and the user also doesn't know the skin condition after applying.

Therefore, there is a need to provide an improved personalization skin care product system, method and computer program product, so as to solve the aforementioned problems.

SUMMARY OF THE INVENTION

An object of the present invention is to provide a personalization skin care product system, comprising: a measuring device and a processor. The measuring device is for measuring a user's skin information; the processor executes a computer program product for providing a personalization suggestion message according to the user's skin information; wherein, the personalization suggestion message corresponds to a user controllable interface of an adjustable skin care product device, wherein the adjustable skin care product device provides a personalization skin care product with different volume proportion of the ingredients according to the different instructions from the user controllable interface.

Thus, the personalization skin care product system can provide the suggestion to the user according the user's skin condition, and the user controllable interface can be controlled based on the suggestion, so that the adjustable skin care product device can provide a suitable skin care product to the user.

Another object of the present invention is to provide a computer program product for a personalization skin care product system. The computer program product is executed by a processor and comprises at least one program code for providing: an instruction, enabling the processor to receive a user's skin information measured by a measuring device; and an instruction, enabling the processor to provide a personalization suggestion message according to the user skin information; wherein, the personalization suggestion message corresponds to a user controllable interface of an adjustable skin care product device, wherein the adjustable skin care product device provides a personalization skin care product with different volume proportion of the ingredients according to the different instruction from the user controllable interface.

Another object of the present invention is to provide a personalization skin care product method executed by a personalization skin care product system. The personalization skin care product method comprises the steps of: measuring a user's skin information by a measuring device; and providing a personalization suggestion message according to the user's skin information by a processor executing a computer program product; wherein, the personalization suggestion message corresponds to a user controllable interface of an adjustable skin care product device, wherein the adjustable skin care product device provides a personalization skin care product with different volume proportion of the ingredients according to the different instructions from the user controllable interface.

Figure 3A:
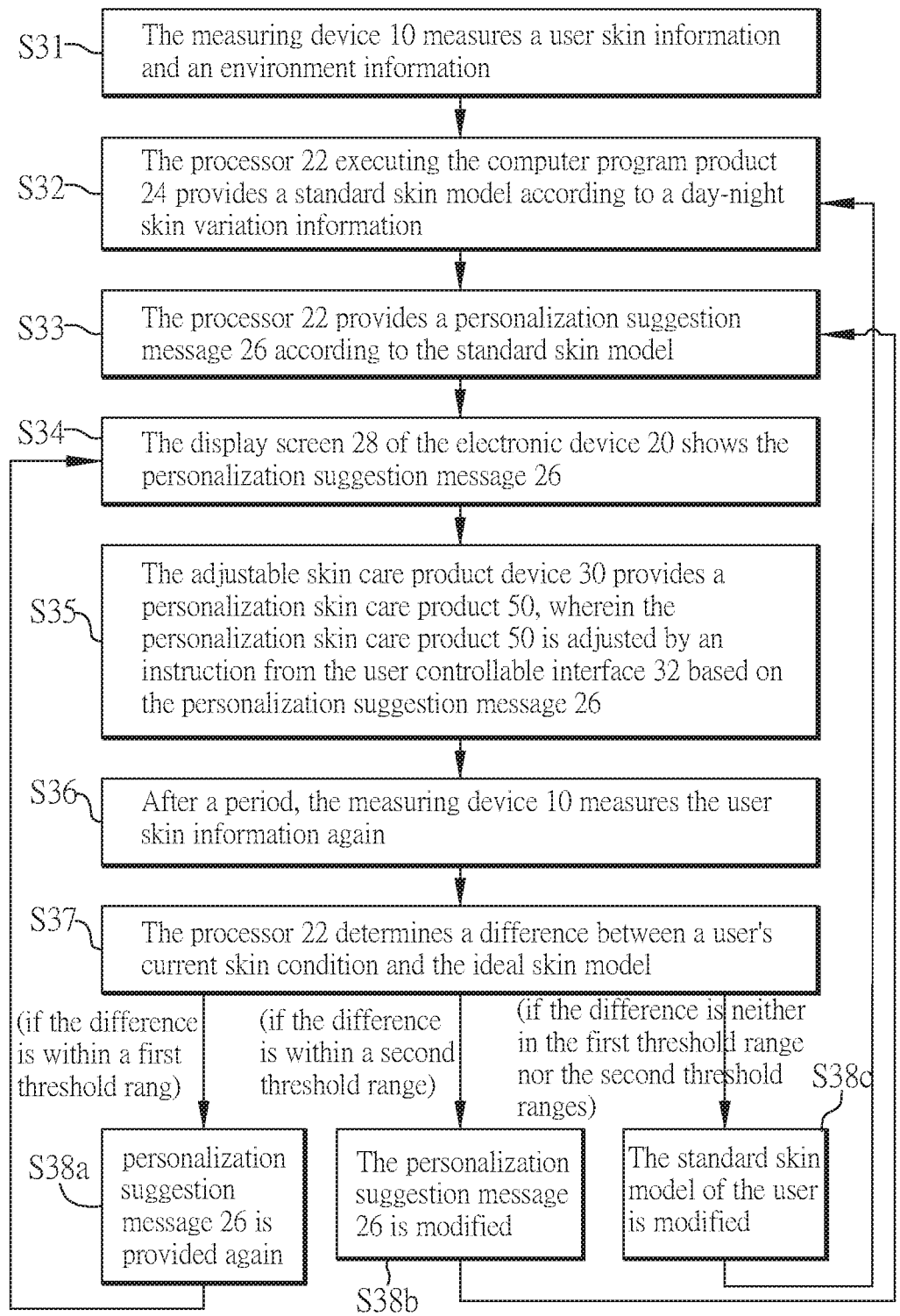
FIG. 3(A) is flow chart of a personalization skin care product method according to an embodiment of the invention.

FIG. B is a flow chart illustrating the detail of the step S37 in FIG. 3(A).

Figure 4A:
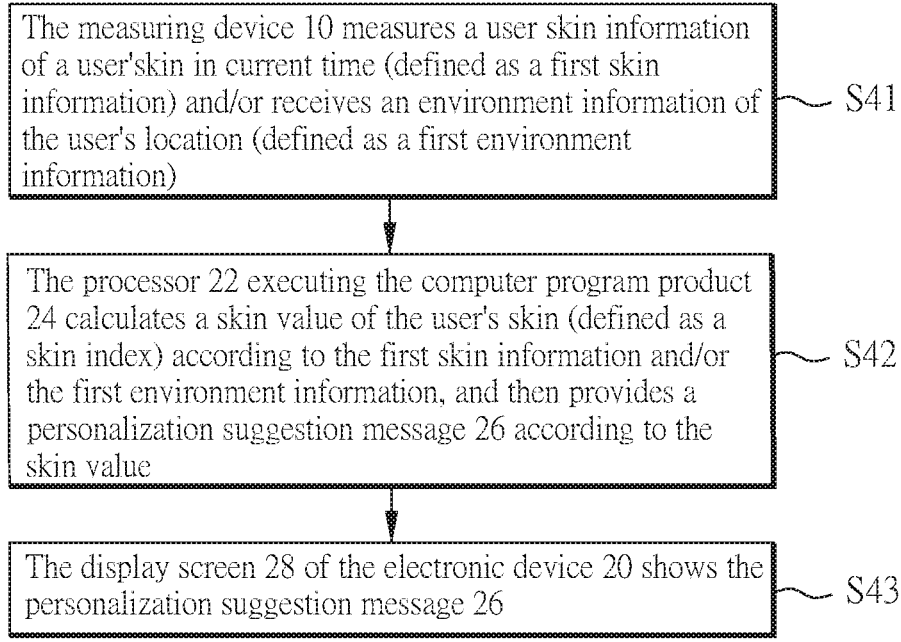
Figure 4B:
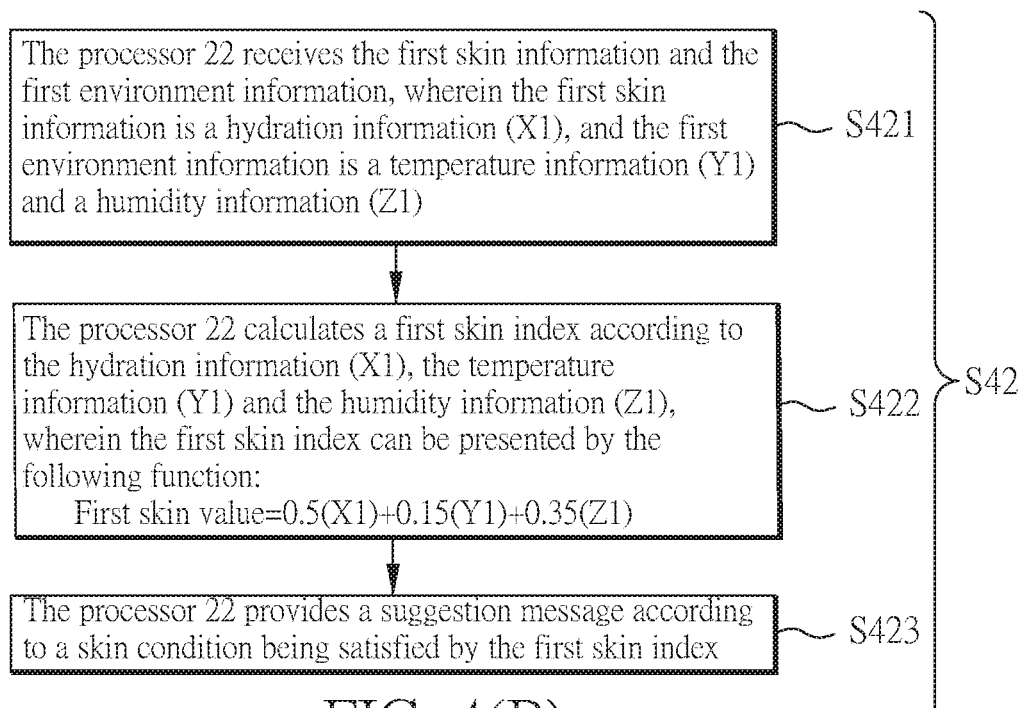

FIG. 4(A) is a flow chart illustrating a method of "providing a personalization suggestion message 26" according to another embodiment of the invention;

FIG. 4(B) is a flow chart illustrating the detail of the step S42 in FIG. 4(A) according to first example.

Figure 4C:
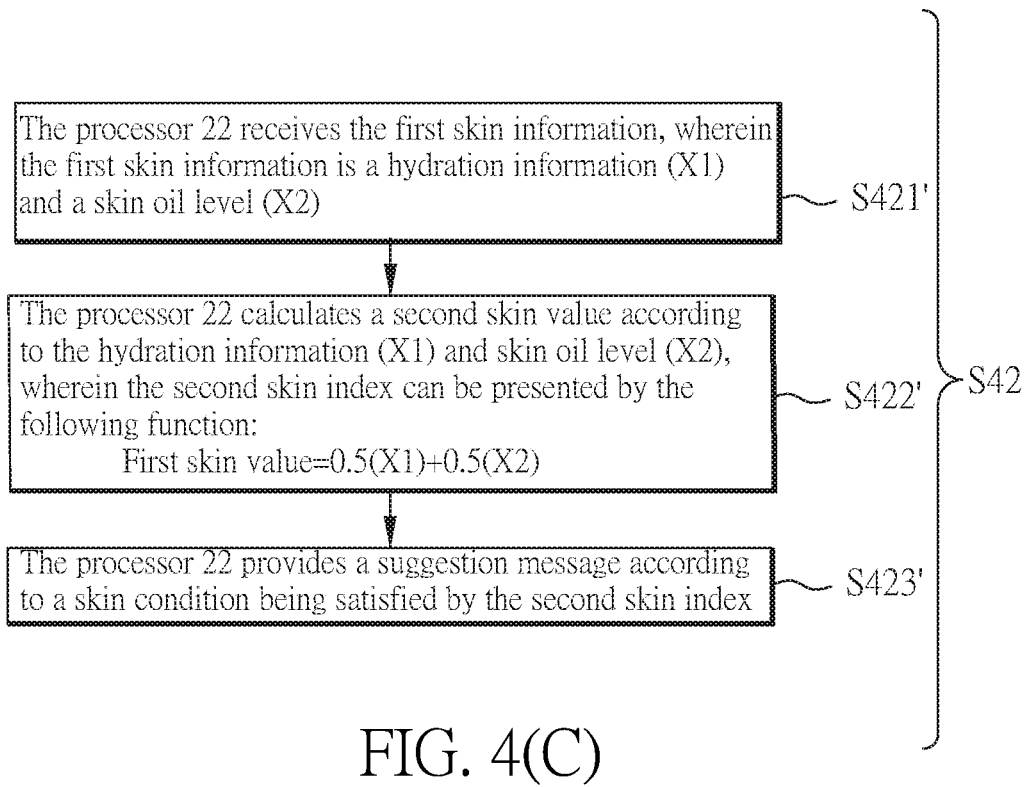

FIG. 4(C) is a flow chart illustrating the detail of the step S42 in FIG. 4(A) according to second example.

DETAILED DESCRIPTION OF THE PREFERRED EMBODIMENT

It is to be noted that, any description hereinafter using "when . . . " or "at the time of . . . " is intended to comprise a time "concurrent to, before, or after" the thing indicated by either of the two phrases happens. Besides, when there are more than one effects recited in association with one element, component or assembly, as long as these effects are conjoined by the term "or", any of these effects may be exist independently and the possibility of coexistence of plural such effects is ne excluded. Moreover, in the specification and the appended claims, the recitation of "a particular operation executed by a unit" means the unit can not only execute the particular operation, but also execute other operations. Besides, when there are more than one units recited in association with one element, component or assembly, as long as these units are conjoined by the term "and/or", any of these units may be exist independently and the possibility of coexistence of plural such units is ne excluded.

Figure 1A:
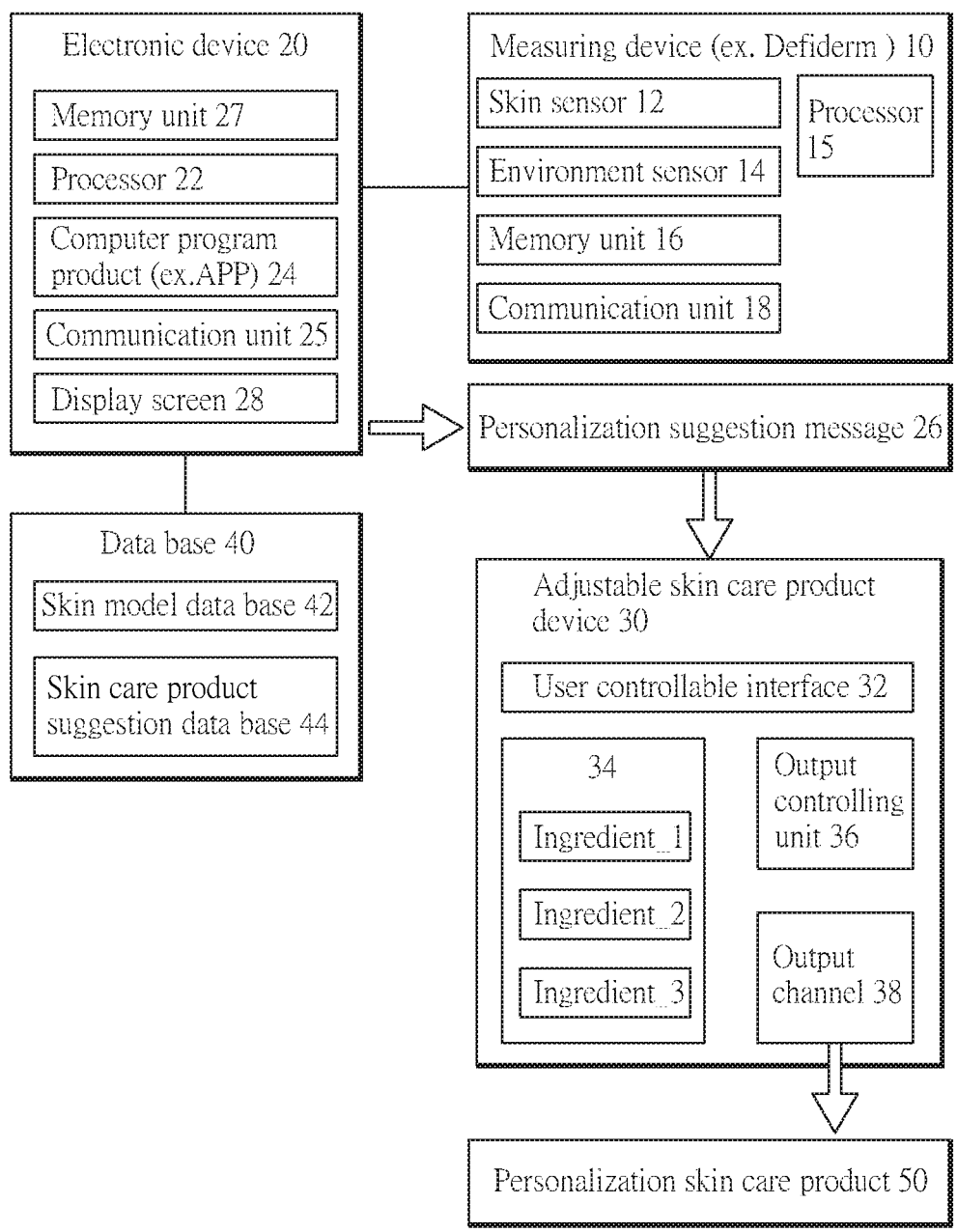
FIG. 1(A) is a schematic diagram of a personalization skin care product system according to an embodiment of the invention.

FIG. 1(A) is a schematic diagram of a personalization skin care product system 1 according to an embodiment of the present invention. As shown in FIG. 1(A), the personalization skin care product system 1 comprises a measuring device 10 and a processor 22, and the processor 22 can execute a computer program product 24. In an embodiment, the personalization skin care product system 1 is combined with an electronic device 20, an adjustable skin care product device 30 and a data base 40, wherein the processor 22 is disposed in the electronic device 20.

The measuring device 10 is for measuring a user's skin information from a user. The processor 22 executing the computer program product 24 is used for providing a personalization suggestion message 26 according to the skin information. The personalization suggestion message 26 corresponds to a user controllable interface 32 of the adjustable skin care product device 30. The adjustable skin care product device 30 provides a personalization skin care product 50 with different volume proportion of the ingredients according to the different instructions from the user controllable interface 32. Thus, the personalization skin care product system 1 can provide the personalization skin care product 50 suitable for the user's skin. In an embodiment, the personalization skin care product 50 may be one skin care product having multiple ingredients. In an embodiment, the personalization skin care product 50 may comprise multiple sub skin care products, and each sub skin care product has multiple ingredients. In an embodiment, the sub skin care products can be serum, lotion, face wash, etc.; while the invention is not limited thereto.

In an embodiment, the measuring device 10 can comprise a skin sensor 12, an environment sensor 14 and a signal processor. The skin sensor 12 is for measuring the signal in relation to skin. The environment sensor 14 is for acquiring the information relating to the environment where the user locates. The processor 15 can analyze the signal measured by the skin sensor 12 or the environment sensor 14, so as to generate the user skin information or the environment information. In an embodiment, the user skin information comprises at least a melanin information, an oxygen level information and/or a hydration information. The environment information comprises at least a temperature information, a humidity information and/or a UV information; while the invention is not limited thereto. Besides, in an embodiment, the measuring device 10 can measure a user's skin oil level information by any possible method.

Besides, the measuring device 10 can further comprise a memory unit 16 and a communication unit 18, wherein the memory unit 16 is for recording the user's skin information and the environment information, and the communication unit 18 is for transmitting the user's skin information and the environment information to other devices, e.g. the electronic device 20 or a network server, etc. More details about the skin sensor 12 and the environmental sensor 14 will be explained in further paragraphs. In addition, the memory unit 16 can be implemented at least by a storage device such as a memory, a hard disk, etc. The communication unit 18 can be implemented at least by a communication device such as a wired communication device, a wireless communication device, etc. Because the details of the memory unit 16 and the communication unit 18 are known to the person skilled in the art, the detailed description therefor is deemed unnecessary.

In an embodiment, the electronic device 20 can be any device having the processor 22, and the electronic device 20 can, by way of example and not limitation, be a smartphone, a desktop computer, a notebook computer, a tablet computer, a wearable device, a network server, etc. The processor 22 can be a microprocessor, a microcontroller or a device having similar functions, etc. In an embodiment, the electronic device 20 further comprises a communication unit 25, a memory unit 27 and a display screen 28, wherein the communication unit 25 is for receiving the user's skin information and the environment information from the measuring device 10, and the memory unit 27 is for recording the user's skin information and the environment information, and the display screen 28 is for showing the personalization suggestion message 26. Besides, the computer program product 24 can also be stored in the memory unit 27, and thus the computer program product 24 can be executed by the processor 22. The processor 22 can comprise at least one program code in order to provide at least one instruction to enable the processor 22 to analyze the user's skin information and the environment information, and thus provide the personalization suggestion message 26. More details about "analyze the user's skin information and the environment information" will be explained in further paragraphs. Besides, because the details of the communication unit 25, the memory unit 27 and the display screen 28 are known to a person skilled in the art, a detailed description therefor is deemed unnecessary.

In an embodiment, the computer program product 24 can comprise a plurality of program codes, wherein each program code can enable the processor 22 to execute a particular operation. In an embodiment, the said program codes can, by way of example and not limitation, be sub programs of a main program. In an embodiment, the computer program product 24 can be stored in a non-transitory computer readable medium, e.g. a memory, a hard disc, an optical disc, a USB flash drive, an online disk, a network server, etc. Besides, in an embodiment, the computer program product 24 can be implemented as software, e.g. APP, computer software, etc. More details about the computer program product 24 will be explained in further paragraphs.

In an embodiment, the data base can comprise a skin model data base 42 and a skin care product suggestion data base 44. The skin model data base 42 can store a plurality of skin models and at least one ideal skin model. The skin care product suggestion data base 44 can store a plurality of suggestion messages. Each suggestion message corresponds to at least one skin model, skin value or skin condition. More details about the skin models and the suggestion messages will be explained in further paragraphs. Besides, the data base 40 can be disposed in the electronic device 20. However, the data base 40 can also be dispose out of the electronic device 20, for example, the data base 40 can be disposed in a network server. Besides, a program code of the computer program product 24 can provide an instruction for enabling the processor 22 to connect to the data base 22.

Figure 1B:
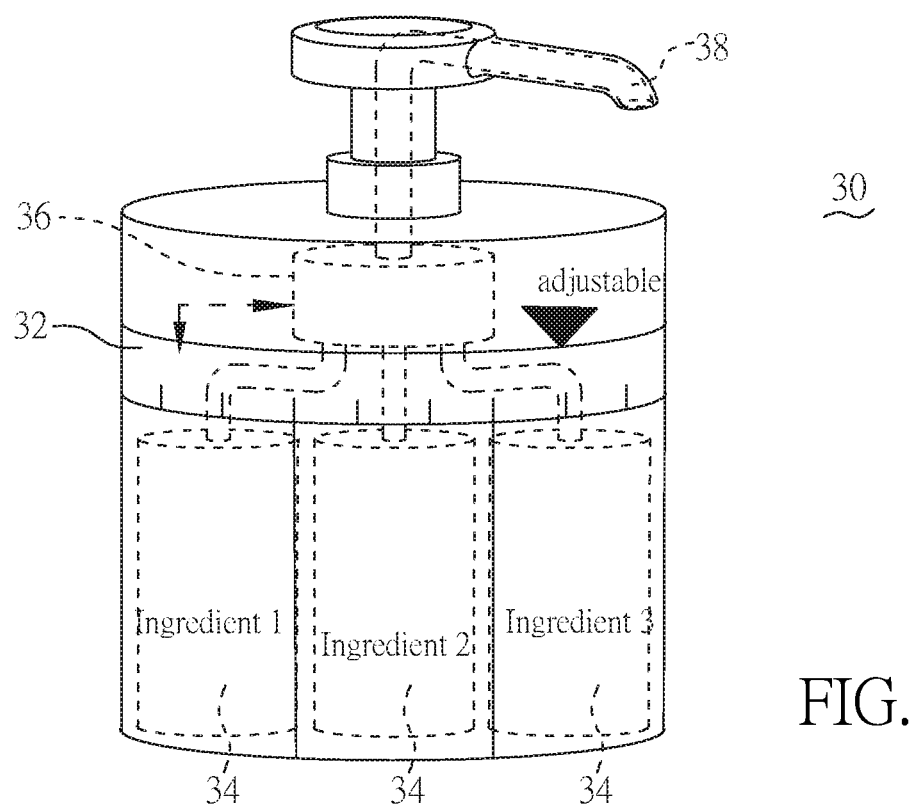
FIG. 1(B) is a schematic diagram of the adjustable skin care product device according to an embodiment of the invention.
Figure 1C:
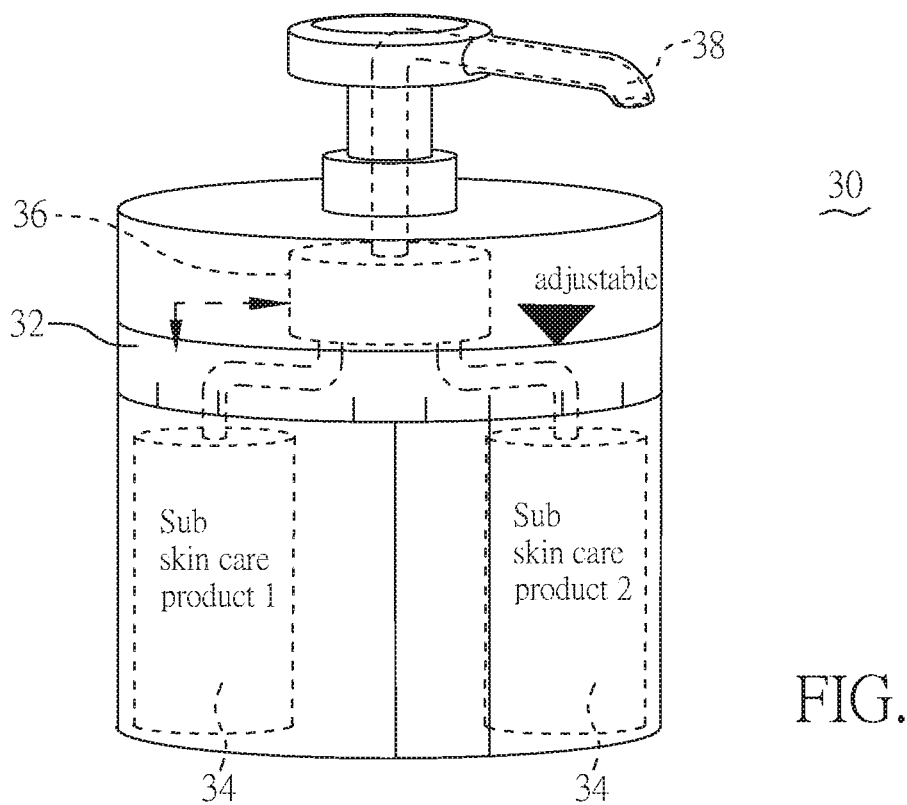
FIG. 1(C) is another schematic diagram of the adjustable skin care product device according to an embodiment of the present invention.

FIG. 1(B) is a schematic diagram of the adjustable skin care product device 30 according to an embodiment of the present invention. FIG. 1(C) is another schematic diagram of the adjustable skin care product device 30 according to an embodiment of the present invention. Please refer to FIG. 1(A) to FIG. 1(C).

As shown in FIGS. 1(A) and 1(B), the adjustable skin care product device 30 can comprise a cover and an inner space, wherein the inner space stores a plurality of ingredients of the personalization skin care product 50. As shown in FIGS. 1(A) and 1(C), the adjustable skin care product device 30 can comprise a cover and an inner space, wherein the inner space stores a plurality of sub skin care products. In an embodiment, the adjustable skin care product device 30 can comprise the user controllable interface 32, an ingredient storage area 34, an output controlling unit 36 and an output channel 38.

The user can input a control instruction to the adjustable skin care product device 30 by using the user controllable interface 32, thereby adjusting the volume proportion of the ingredients of the personalization skin care product 50. The recitation "adjusting the volume proportion of the ingredients" can be "adjusting the volume proportion of multiple ingredients of one skin care product" or "adjusting the volume proportion of multiple sub skin care products". The ingredient storage area 34 can be divided into multiple sub-areas. In an embodiment, each sub-area of the ingredient storage area 34 can store one ingredient (as shown in FIG. 1(B)); in another embodiment, each sub-area of the ingredient storage area 34 can store one sub skin care product (as shown in FIG. 1(C)). Each sub-area is separated from each other, and each sub-area is connected with the output channel 38, respectively; while the invention is not limited thereto. The output control unit 36 can adjust the volume of each ingredient (or each sub skin care product) entering the output channel 38 from the ingredient storage area 34 based on the instruction from the user controllable interface 32. The output channel 38 can output the ingredients (or the sub skin care products), wherein the ingredients (or the sub skin care products) can be mixed to form the personalization skin care product 50. In an embodiment, the output channel 38 outputs one ingredient (or one sub skin care product) at a time, but in another embodiment, the ingredients (or the sub skin care products) can be mixed in the output channel 38 before being outputted. Besides, in an embodiment, each sub-area can be provided with a flow control valve, and the output control unit 36 can adjust the volume of each ingredient (or each sub skin care product) entering the output channel 38 by controlling the flow control valves; while the invention is not limited thereto. Since the detailed structure of the adjustable skin care product device 30 is not the focus of the present invention, a detailed description therefor is deemed unnecessary.

Figure 2A:
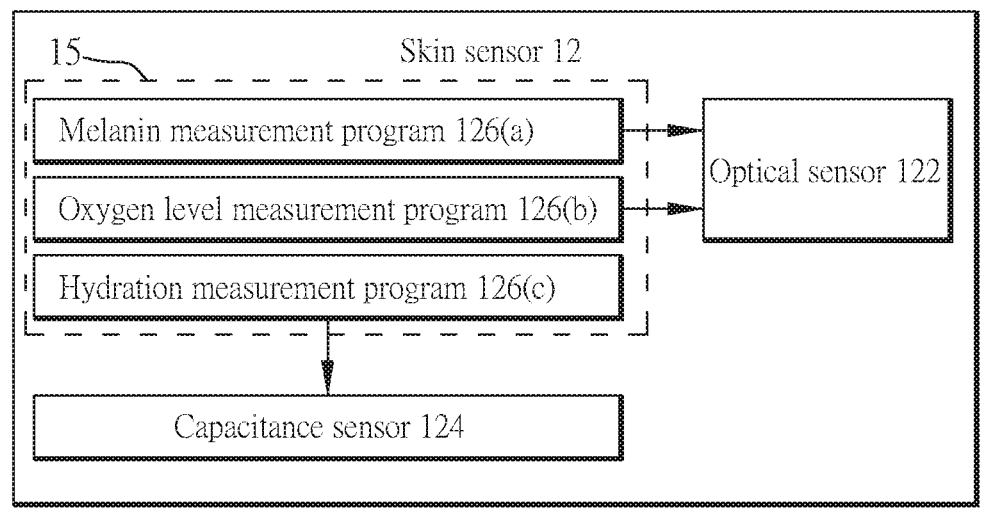
FIG. 2(A) is a schematic diagram illustrating the detail structure of the skin sensor according to an embodiment of the invention.

Next, the details of the skin sensor 12, the environment sensor 14, the computer program product 24, the skin model data base 42 and the skin care product suggestion data base 44 will be described. Please refer to FIG. 1 to FIG. 2(E) at the same time The detail of the skin sensor 12 will be described herein. FIG. 2(A) is a schematic diagram illustrating the detailed structure of the skin sensor 12 according to an embodiment of the invention. As shown in FIG. 2(A), the skin sensor 12 can comprise an optical sensor 122 and/or a capacitance sensor 124. In an embodiment, the melanin information and the oxygen level information can be measured by the optical sensor 122, and the hydration information can be measured by the capacitance sensor 124. In an embodiment, the optical sensor 122 and the capacitance sensor 124 are connected to the processor 15. Therefore, when an optical signal or an electric signal is measured by the optical sensor 122 or the capacitance sensor 124, the processor 15 can execute a signal processing to transform the optical signal or the electric signal into the melanin information, oxygen level information or the hydration information. Besides, the optical sensor can comprise a light emitter and a light receiver.

As shown in FIG. 2(A), in an embodiment, the processor 15 can execute a melanin measurement program 126(a) to transform the optical signal into the melanin information. Because the melanin in the skin tissue can absorb a light with a wavelength of about 520 nm, the processor 15 can acquire an intensity information of other reflected lights with different wavelengths in the skin tissue, e.g. the intensity information of green light with a wavelength of about 519 nm, the red light with a wavelength of about 660 nm and the infrared light with a wavelength of about 940 nm, and the processor 15 can execute the melanin measurement program 126(a) to transform the intensity information into the user's melanin information; while the invention is not limited thereto.

In an embodiment, the melanin measurement program 126(a) can be presented in the following function:

$$MI = \frac{500}{\log 5(\log \text{ infrared} - \log \text{ red}) + 500},$$

wherein, MI is the melanin information, infrared is the intensity of the infrared light, red is the intensity of the red light. Thus, the melanin information can be measured by the measuring device 10.

Please refer to FIG. 2(A) again. In an embodiment, the signal processor 125 can execute an oxygen level measurement program 126(b) to acquire the oxygen level information. The hemoglobin can be categorized into oxyhemoglobin (for carrying oxygen) and deoxyhernoglobin (not for carry oxygen), wherein the oxyhemoglobin can absorb the light with a wavelength of about 660 nm, and deoxyhemoglobin can absorb the light with a wavelength of about 940 nm. Therefore, the optical sensor 122 can acquire the information indicating the ratio of the light with said wavelengths in the user's blood by the optical sensor 122, and the signal processor 125 can execute the oxygen level measurement program 126(b) to transform the said information into the user's oxygen level information; while the invention is not limited thereto.

In an embodiment, the oxygen level measurement program 126(b) can be presented in the following function:)

$$\Delta[HbR] = \frac{\varepsilon_{HbO2}(\lambda_2)\Delta\mu_a(\lambda_1) - \varepsilon_{HbO2}(\lambda_1)\Delta\mu_a(\lambda_2)}{\varepsilon_{HbR}(\lambda_1)\varepsilon_{HbO2}(\lambda_2) - \varepsilon_{HbO2}(\lambda_1)\varepsilon_{HbR}(\lambda_2)}$$

$$\Delta[HbO2] = \frac{\varepsilon_{HbR}(\lambda_1)\Delta\mu_a(\lambda_2) - \varepsilon_{HbR}(\lambda_2)\Delta\mu_a(\lambda_1)}{\varepsilon_{HbR}(\lambda_1)\varepsilon_{HbO2}(\lambda_2) - \varepsilon_{HbO2}(\lambda_1)\varepsilon_{HbR}(\lambda_2)},$$

wherein $\Delta[HbR]$ is light concentration of deoxyhemoglobin, $\Delta[HbO2]$ is light concentration of oxyhemoglobin, $\varepsilon_{HbR}$ is extinction coefficient of deoxyhemoglobin, $\varepsilon_{HbO2}$ is extinction coefficient of oxyhemoglobin, is light absorbed intensity, $\lambda_1$ is 660 nm (nanometer), and $\lambda_2$ is 940 nm.

Besides, $\epsilon_{HbO2}$ and $\Delta\mu_a$ can be preset in the measuring device 10. Thus, the skin sensor 12 can measure the oxygen level information.

Besides, in an embodiment, the processor 15 can execute a hydration measurement program 126 (*c*) to acquire the a hydration information. Since the different mediums has different dielectric coefficient, for instance, the dielectric coefficient is about 1 for air and about 80 for water respectively, the capacitance value of the user's skin is higher when the user's hydration is higher. Accordingly, the capacitance sensor 124 can measures the capacitance of the user's skin, and the processor 15 can execute the hydration measurement program 126 (*c*) to transform the capacitance of the user's skin into the hydration information.

Figure 2B:
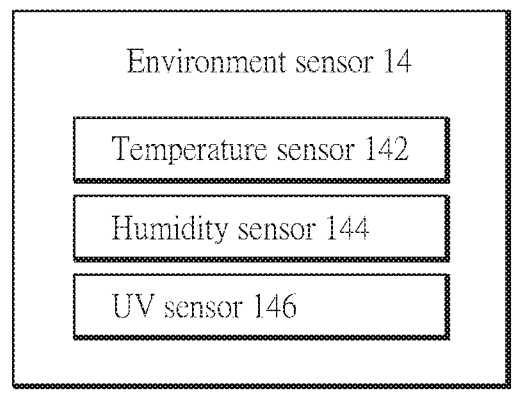
FIG. 2(B) is a schematic diagram illustrating the detail structure of the environment sensor according to an embodiment of the invention.

Next, the detail of the environment sensor 14 will be described. FIG. 2(B) is a schematic diagram illustrating the detailed structure of the environment sensor 14 according to an embodiment of the present invention. As shown in FIG. 2(B), the environment sensor 14 comprises a temperature sensor 142 and/or a humidity sensor 144. The temperature sensor 142 is for measuring the temperature information, and the humidity sensor 144 is for measuring the humidity information. Besides, the environment sensor 14 can also comprise a UV sensor 146 for measuring the UV information, while the present invention is not limited thereto. Besides, in an embodiment, the environment sensor 14 can download the environment information from a network server, directly.

Next, the details of the program codes of the computer program product 24 and the data base 40 will be described. Please refer to FIG. 2(C) and FIG. 2(D), the FIG. 2(C) is a schematic diagram illustrating a detailed structure of the computer program product 24 according to an embodiment of the present invention, and the FIG. 2(D) is a schematic diagram illustrating a detailed structure of the data base 40 according to an embodiment of the present invention.

Figure 2C:
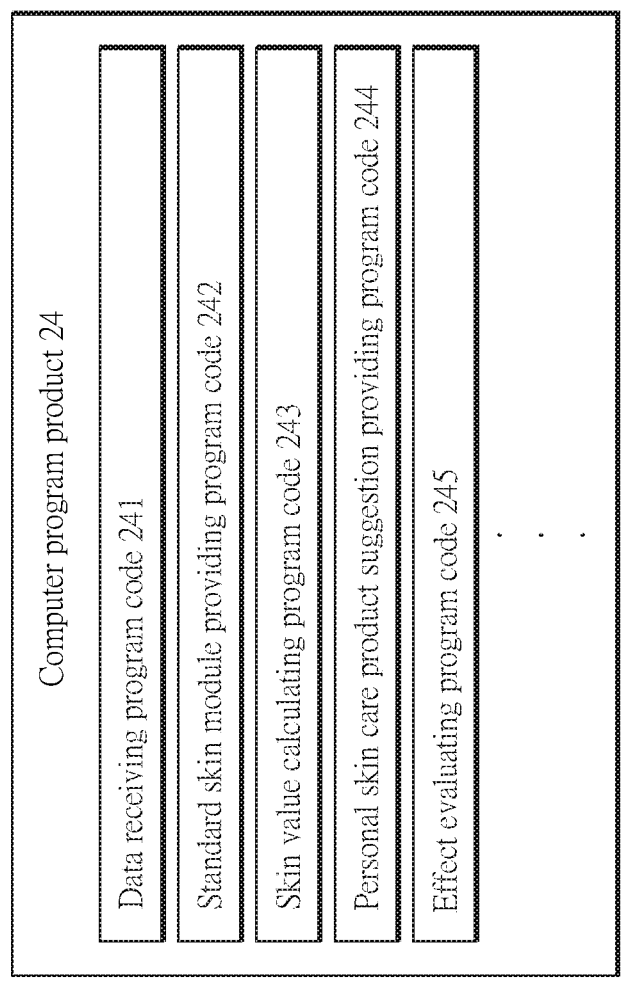
FIG. 2(C) is a schematic diagram illustrating a detail structure of the computer program product according to an embodiment of the invention.
Figure 2D:
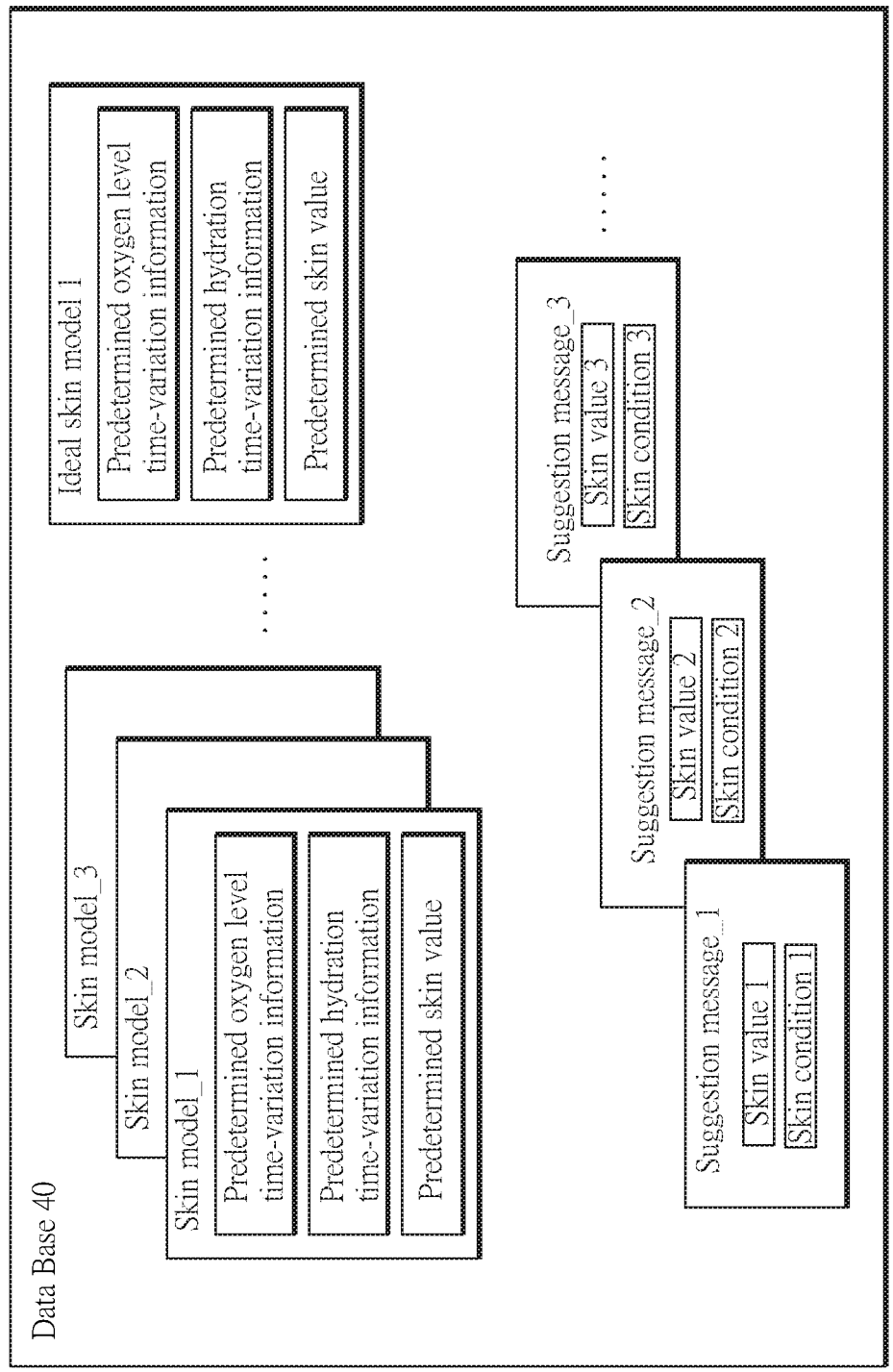
FIG. 2(D) is a schematic diagram illustrating a detail structure of the data base according to an embodiment of the invention.

As shown in FIG. 2(C), the computer program product 24 comprises a data receiving program code 241, a standard skin model providing program code 242, a skin value calculating program code 243, a personal skin care product suggestion providing program code 244 and an effect evaluating program code 245. And as shown in FIG. 2(D), the data base 40 stores a plurality of skin models, a plurality of suggestion message and at least one ideal skin model, wherein each of the skin model and the ideal skin model corresponds to a predetermined hydration time-variation information, a predetermined oxygen level time-variation information and a predetermined melanin time-variation information, respectively. Each suggestion message corresponds to a skin value or a skin condition. In an embodiment, each skin model is defined as a type of skin, e.g. oily skin, dry skin, mixed skin, etc., and the ideal skin model is defined as a predetermined ideal type of skin, e.g. neutral skin; while the invention is not limited thereto. When the user's skin value is determined, the processor 22 can provide the personalization suggestion message 26 to the user, and the processor 22 can determine the effect of the personalization skin care product 50 by comparing a difference between the user's skin (after using the personalization skin care product 50) and the standard skin model. It is noted that each program code 241~245 provides at least one instruction to enable the processor 22 to execute particular operations.

Figure 2E:
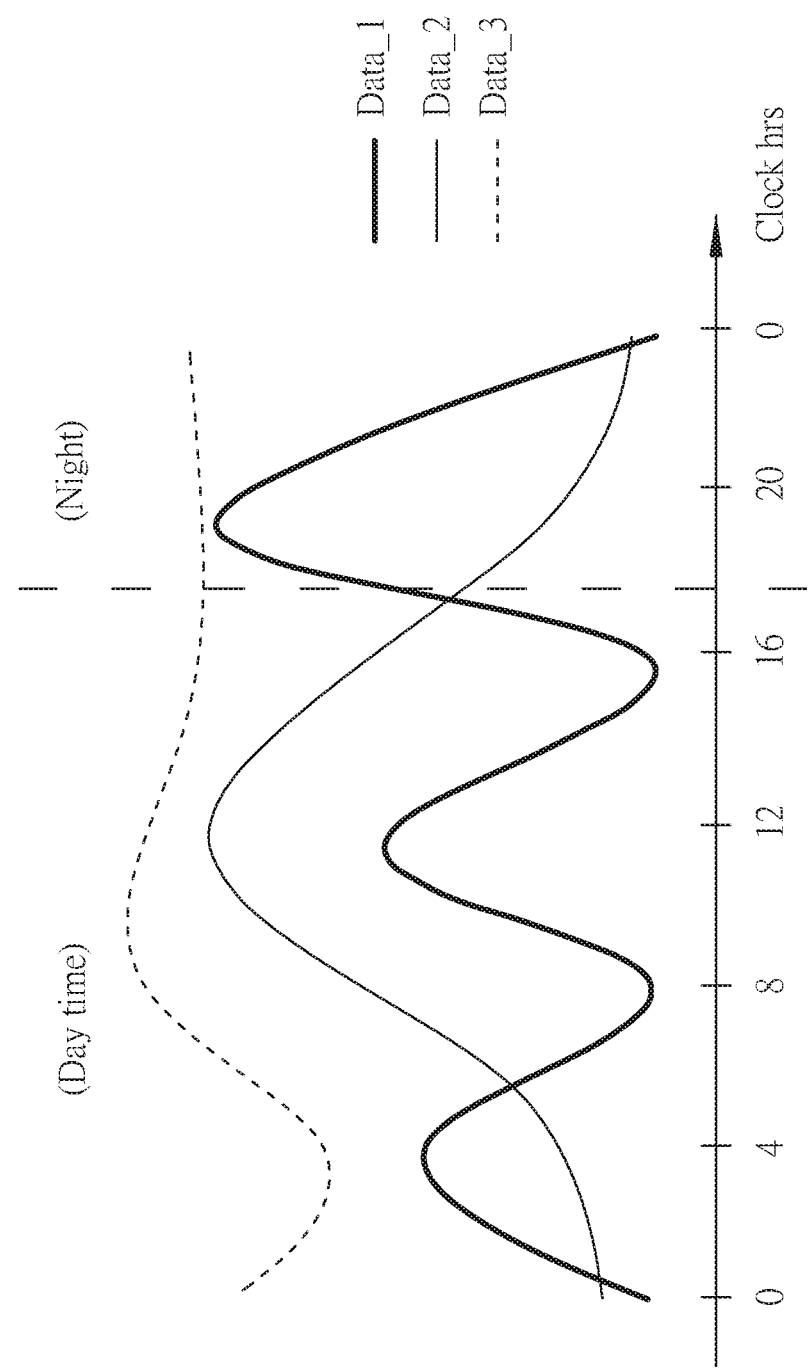
FIG. 2(E) is a schematic diagram illustrating the predetermined hydration information, the predetermined oxygen level information, and the predetermined skin oil level information corresponding to the skin models according to an embodiment of the invention.

FIG. 2(E) is a schematic diagram illustrating the predetermined hydration information, the predetermined oxygen level information, and the predetermined skin oil level information corresponding to the skin models (or the ideal skin model) according to an embodiment of the invention. As shown in FIG. 2(E), the predetermined hydration time-variation information (data_1) is formed by a plurality of predetermined hydration information corresponding to different time points respectively; the predetermined oxygen level time-variation information (data_2) is formed by a plurality of predetermined oxygen level information corresponding to different time points, respectively; the predetermined skin oil level time-variation information (data_3) is formed by a plurality of predetermined skin oil level information corresponding to different time points, respectively. Each predetermined hydration time-variation information (data_1), each predetermined oxygen level time-variation information (data_2) and each predetermined skin oil level time-variation information (data_3) of the skin model or the ideal skin model can be stored in the data base 40. Besides, regarding the ideal skin model, the predetermined hydration time-variation information (data_1) can indicate the ideal hydration at each time point, the predetermined oxygen level time-variation information (data_2) can indicate the ideal oxygen level at each time point, and predetermined skin oil level time-variation information (data_3) can indicate the ideal skin oil level at each time point. In addition, the information of the said ideal hydration, ideal oxygen level and ideal skin oil level can be preset in the electronic device 20.

In an embodiment, the data receiving program code 241 can enable the processor 22 to receive the user's skin information and the environment information from the measuring device 10; while the invention is not limited thereto.

In an embodiment, the standard skin model providing program code 242 can enable the processor 22 to generate a day-night skin variation information according to the user's skin information and the environment information, and can enable the processor 22 to set a skin model in the data base 40 as the standard skin model. In detail, the day-night skin variation information can be defined as a hydration time-variation information, an oxygen level time-variation information and a skin oil level time-variation information. Because each skin model corresponds to one predetermined hydration time-variation information, one predetermined oxygen level time-variation information and one predetermined skin oil level time-variation information, the processor 22 can search a similar skin model among the skin models in the data base 40 according to the day-night skin variation information and sets the similar skin model as the standard skin model; while the invention is not limited thereto.

In an embodiment, the skin value calculating program code 243 can enable the processor 22 to calculate the user's skin value according to the predetermined oxygen level time-variation information of the standard skin model, the predetermined hydration time-variation information of the standard skin model, the environment information and the latest measured user's skin information. In another embodiment, the skin value calculating program code 243 can enable the processor 22 to calculate the user's skin value according to a skin information of the user's skin in current time and/or an environment information in current time. While the invention is not limited thereto.

In an embodiment, the personal skin care product suggestion providing program code 244 can enable the processor 22 to search a suggestion message corresponding to the user's skin value in the data base 40, and sets the suggestion message as the personalization suggestion message 26. In an embodiment, each suggestion message corresponds to a skin value or a skin condition, and thus when the user's skin value is calculated, the processor 22 can find one skin value corresponding to the user's skin value or one skin condition matched with the user's skin value from the data base 40, so as to provide a suitable suggestion message to the user; while the invention is not limited thereto.

In an embodiment, the effect evaluating program code 245 can enable the processor 22 to evaluate the effect of the personalization suggestion message 26. For example, after the user continues to use the personalization skin care product 50, the processor 22 can evaluate the difference between the user's skin and the ideal skin model so as to evaluate the effect of the personalization suggestion message 26 (i.e. the effect of the personalization skin care product 50); while the invention is not limited thereto.

In an embodiment, each personalization suggestion message 26 corresponds to one operating instruction of the user controllable interface 32, wherein the different operating instruction can make the adjustable skin care product device 30 to output the personalization skin care product 50 with different volume proportion of the ingredients, e.g. to output the personalization skin care product 50 with different volume proportion of the sub skin products. Thus, the user can follow the operating instruction of the personalization suggestion message 26 to control the user controllable interface 32.

Next, the operation of the personalization skin care product system 1 will be described. FIG. 3(A) is a flow chart of a personalization skin care product method according to an embodiment of the present invention, wherein the personalization skin care product method is executed by the personalization skin care product system 1 in FIG. 1(A) to FIG. 1(D), and the processor 22 of the electronic device 20 executes the computer program product 24.

First, step S31 is executed in which, the measure device 10 measures the user's skin information and the environment information of the user's location. Then, step S32 is executed in which, the processor 22 executes the computer program product 24 to provide the standard skin model for the user according to the user's day-night skin variation information. Then, step S33 is executed in which, the processor 22 provides the personalization suggestion message 26 according to the standard skin model. Then, step S34 is executed in which, the display screen 28 shows the personalization suggestion message 26. Then, step S35 is executed, the adjustable skin care product device 30 provides a personalization skin care product 50, wherein the volume proportion of the ingredients of the personalization skin care product 50 is adjusted by the user controllable interface 32 according to the instruction of the personalization suggestion message 26. Then, after a period of time, step S36 is executed, and the measure device 10 measures the user's skin information again. Then, step S37 is executed in which, the processor 22 determines a difference between the user's skin condition and the ideal skin model. If the difference is within a first threshold range, the step S38(*a*) will be executed in which, the personalization suggestion message 26 will be provided again, and the step S34 will be executed again; if the difference is within a second threshold range, the step S38(*b*) will be executed in which, the personalization suggestion message 26 will be modified, and the step S33 will be executed again; if the difference is neither within the first threshold range nor the second threshold range, step S38(*c*) will be executed in which, the standard skin model will be modified, and the step S32 will be executed again; or step S38(*c*) will be executed in which, the processor provides a suggestion of "changing another skin care product device (30) with another skin care product".

The step S31 will be described in more detail. The measuring device 10 measures the user's skin information, wherein the user's skin information can comprise the melanin information, the hydration information and/or the oxygen level information; it is noted that the user's skin information can also comprise other skin characteristics, or the user's skin information can be other skin characteristics. Besides, the measuring device 10 can store the melanin information, the hydration information and/or the oxygen level information by the memory unit 16, and can transmit the melanin information, the hydration information and/or the oxygen level information to the electronic device 20 by the communication unit 18.

Figure 3B:
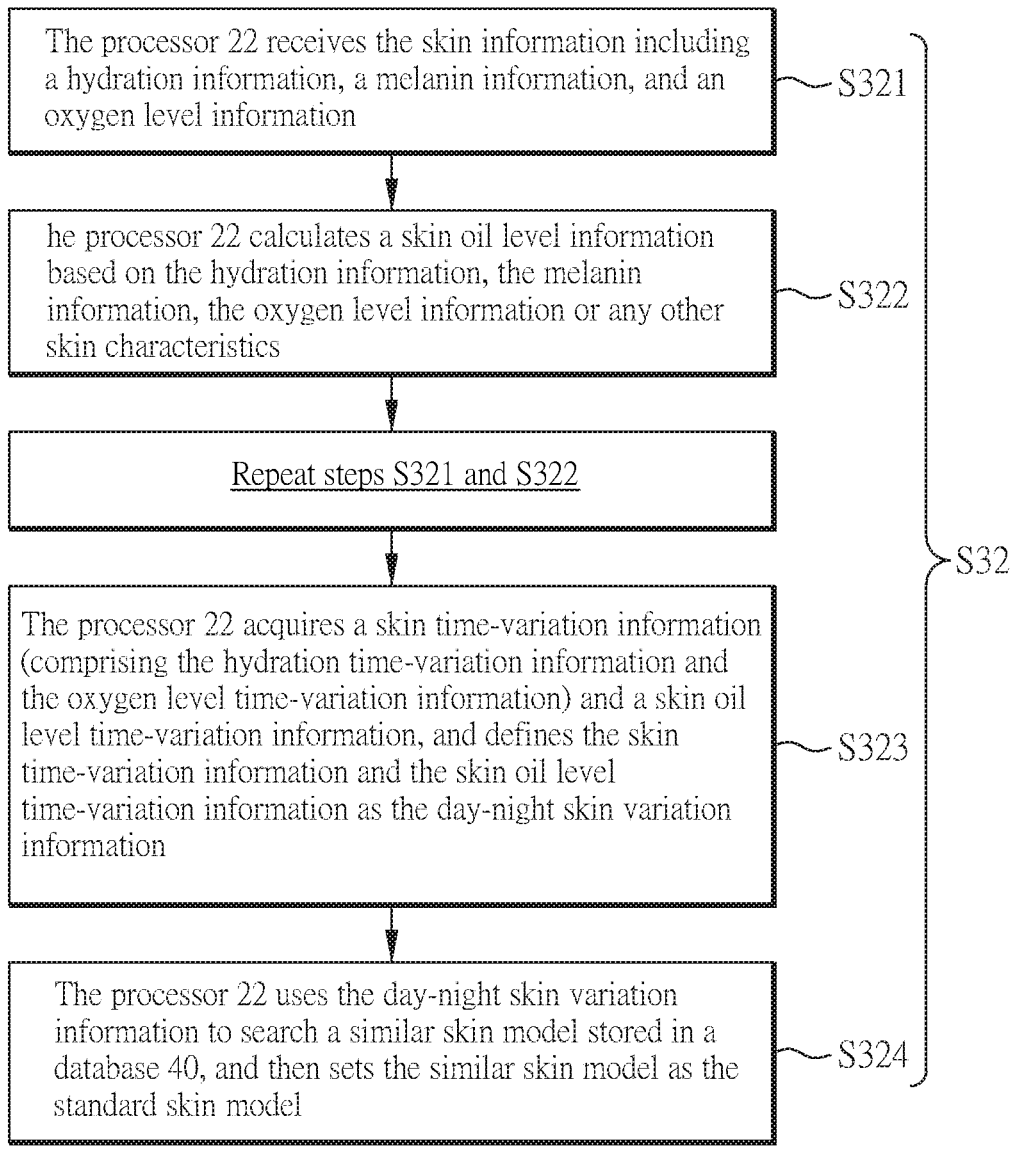
FIG. 3(B) is a flow chart illustrating the detail of the step S32 in FIG. 3(A)

Then, the detail of the step S32 will be described. Please refer to FIG. 3(A) and FIG. 3(B), the FIG. 3(B) is a flow chart illustrating the detail of the step S32 in FIG. 3(A) according to an embodiment.

First, step S321 is executed in which, the processor 22 receives the user skin information from the measuring device 10.

Then, step S322 is executed in which, the processor 22 calculates a skin oil level information according to the melanin information, the hydration information and the oxygen level information. Then, the step S321 and the step S322 are repeated until the repeat times met a certain number; in detail, the measuring device 10 measures a plurality of user's skin information at different time spots, and the processor 22 calculates a plurality of skin oil level information at different time spots according to the user's skin information measured at different time spots. In an embodiment, the certain number comprises at least once in the daytime, and at least once in the nighttime. The specific time period of the day and the night can be preset in the electronic device 20.

Besides, in an embodiment, the processor 22 can calculate the skin oil level information by any suitable implement method.

In an example, the skin oil level can be calculated by the following function:

$$\text{Skin oil level} = (a[\text{frequency1}] - b[\text{frequency2}])/c[\text{frequency3}]$$

wherein, frequency1 is a frequency transformed from a capacitance measured (e.g. measured by the capacitance sensor 124) in current time, frequency2 is a frequency transformed from a capacitance measured (e.g. measured by the capacitance sensor 124) after the user's face skin is washed, frequency3 is average frequency of other user with the same skin condition (Frequency 3 can be pre-stored in the data base 40), and a, b, c is a coefficient (e.g. weight value) of frequency1, frequency2 and frequency3, respectively.

Then, step S323 is executed in which, the processor 22 acquires the plurality of hydration information measured at different time spots (forming the hydration time-variation information), the plurality of oxygen level information measured at different time spots (forming the oxygen level time-variation information) and the plurality of skin oil level information at different time spots (forming the skin oil level time-variation information), and then defines the hydration time-variation information, the oxygen level time-variation information and the skin oil level time-variation information as the thy-night skin variation information.

Thereafter, step S324 is executed, the processor 22 uses the day-night skin variation information to search the similar skin model stored in the database 40, and then sets the similar skin model as the standard skin model.

In an embodiment, the processor 22 can execute a RMSD (Root-Mean-Square Deviation) calculation to compare the user's day-night skin variation information with a predetermined day-night skin variation information (i.e. the predetermined hydration time-variation information, the predetermined oxygen level time-variation information and the predetermined skin oil level time-variation information) of each skin model stored in the data base 40 so as to search the similar skin model having a minimum RMSD result. In a preferable embodiment, the RMSD calculation corresponding to one skin model can be described in the following function:

$$RMSD = a_1 \sqrt{\frac{\sum_{t=1}^{n}(\bar{y}_{1_t} - y_{1_t})^2}{n}} + a_2 \sqrt{\frac{\sum_{t=1}^{n}(\bar{y}_{2_t} - y_{2_t})^2}{n}} + a_3 \sqrt{\frac{\sum_{t=1}^{n}(\bar{y}_{3_t} - y_{3_t})^2}{n}},$$

wherein, RMSD is the result of the RMSD calculation, $\bar{y}_{1_t}$ is the hydration information, $y_{1_t}$ is the predetermined hydration information of the skin model, $\bar{y}_{2_t}$ is the oxygen level information, $y_{2_t}$ is the predetermined oxygen level information of the skin model, $\bar{y}_{3_t}$ is the skin oil level information, $y_{3_t}$ is the predetermined skin oil level information of the skin model, t means time, n is the total number of time, and n is positive integer, and $a_1$, $a_2$, $a_3$ are predetermined weights.

Besides, the processor 22 can execute a RMSD calculation to compare the user's day-night skin variation information with a predetermined day-night skin variation information (i.e. the predetermined hydration time-variation information, the predetermined oxygen level time-variation information and the predetermined skin oil level time-variation information) of the ideal skin model so as to determine the difference between the user's skin and the ideal skin model.

Figure 3C:
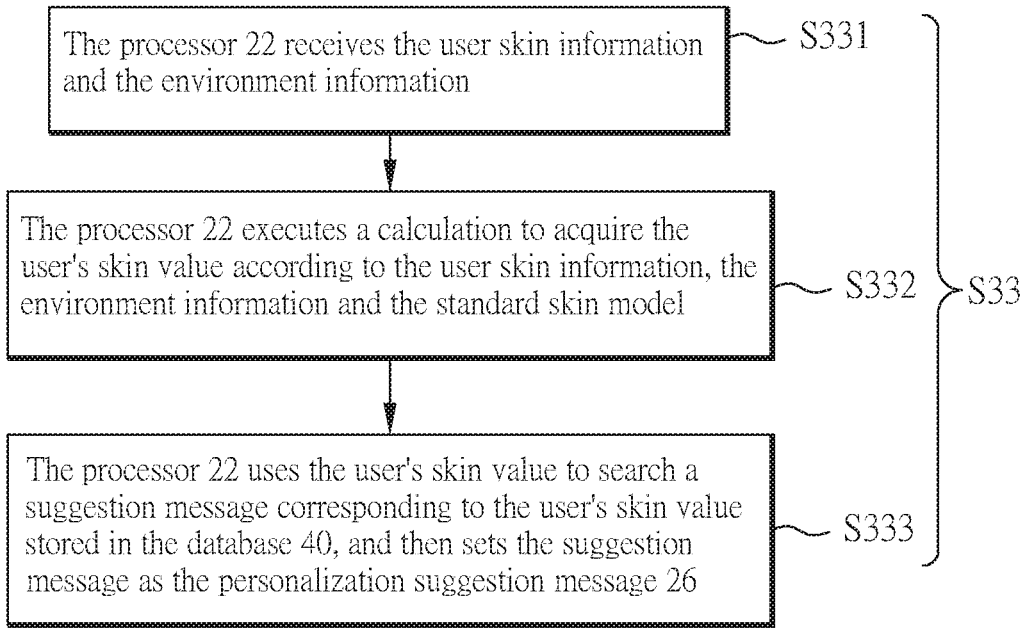
FIG. 3(C) is a flow chart illustrating the detail of the step S33 in FIG. 3(A)

The detail of the step S33 will be described. Please refer to FIG. 3(A) and FIG. 3(C), wherein FIG. 3(C) is a flow chart illustrating the detail of the step S33 in FIG. 3(A).

First, step 331 is executed in which, the processor 22 receives the user's skin information and the environment information. Then, step S332 is executed in which, the processor 22 executes a calculation to acquire the user's skin value according to the user's skin information, the environment information and the standard skin model. Then, step S333 is executed in which, the processor 22 uses the user's skin value to search one suggestion message corresponding to the user's skin value stored in the data base 40, and sets the suggestion message as the personalization suggestion message 26.

In an embodiment, the environment information comprises temperature information and humidity information. In an embodiment, the environment information comprises an indoor temperature information, an outdoor temperature information, an indoor humidity information and/or an outdoor humidity information; while the invention is not limited thereto.

In an embodiment, the calculation for acquiring the user's skin value can be presented by the following function:

skin value=$a(Td+Hd)+b(Tt+Ht)+cM+dM(t)+eO+fO(t)$, wherein skin value is the user's skin value, Td is the indoor temperature information, Hd is the indoor humidity information, Tt is the outdoor temperature information, Ht is the outdoor humidity information, M is the latest measured hydration information, M(t) is the predetermined hydration time-variation information of the standard skin model, O is the latest measured oxygen level information, O(t) is the predetermined oxygen level time-variation information of the standard skin model, a, b, c, d, e, f are predetermined weights corresponding to (Td+Hd), (Tt+Ht), M, M(t), O, O(t); while the invention is not limited thereto.

According to the aforementioned embodiments, each skin value can correspond to one suggestion message stored in the data base 40, and thus the processor 22 can search the suitable suggestion message for the user according to the user's skin value when the user's skin value is acquired. Therefore, the personalization suggestion message 26 can be provided by executing the step S331 to S333.

Besides, in an embodiment, the processor 22 can also determine the difference between the user's skin and the ideal skin model, e.g. the ideal skin model can correspond to a specific skin value, and the processor 22 can analyze the difference between the user's skin value and the specific skin value to determine the difference between the user's skin and the ideal skin model. The analyzation can be implemented by RMSD calculation; while the invention is not limited thereto.

Then, the detail of the step S34 will be described. The processor 22 can control the display screen 28 to show the personalization suggestion message 26, so the user can get the tips for controlling the user controllable interface 32. In another embodiment, the processor 22 can transform the personalization suggestion message 26 into a voice message, and then the voice message is provided through a microphone device.

Figure 3D:
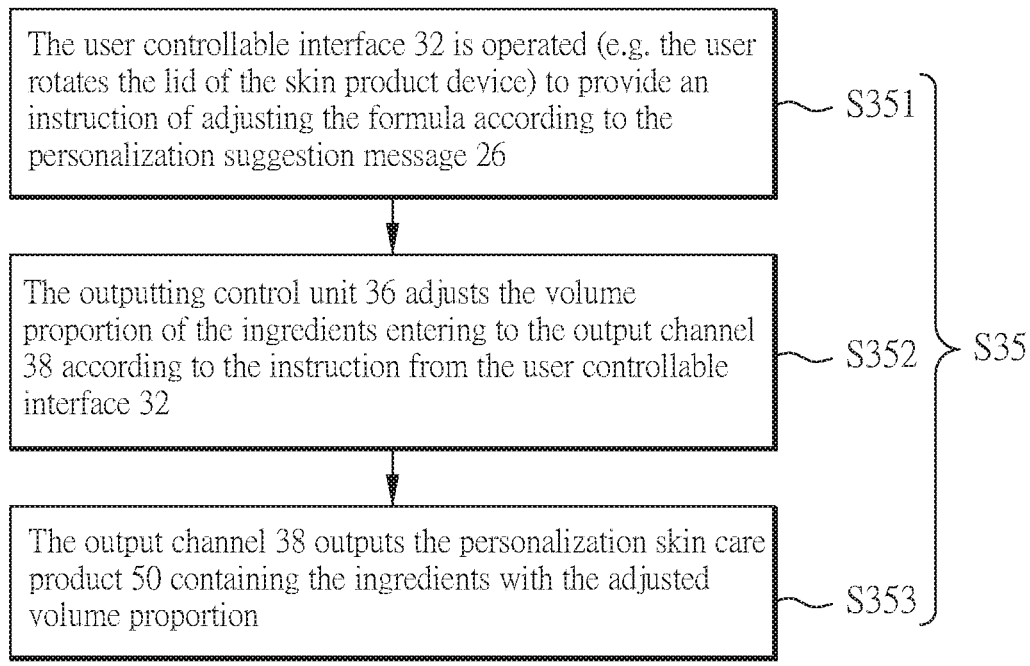
FIG. 3(D) is a flow chart illustrating the detail of the step S35 in FIG. 3(A)

The detail of the step S35 will be described herein. Please refer to FIG. 3(A) and FIG. 3(D), the FIG. 3(D) is a flow chart illustrating the detail of the step S35 in FIG. 3(A).

First, step S351 is executed in which, when the user controllable interface 32 is operated (e.g. when the user rotates a lid of the adjustable skin care product device 30), the user controllable interface 32 can provide the output controlling unit 36 with an instruction of adjusting the formula according to the personalization suggestion message 26. Then, step S352 is executed in which, the output controlling unit 36 adjusts the volume proportion of the ingredients entering the output channel 38 from the sub-areas according to the instruction. Then, step S353 is executed in which, the output channel 38 outputs the personalization skin care product 50. Thus, the adjustable skin care product device 30 can provide the personalization skin care product 50 to the user.

Then, the detail of the step S36 will be described. After the user continues to use the personalization skin care product 50 for a particular period of time, the user can use the measuring device 10 again (i.e. the measuring device 10 can measure a plurality of renew hydration information, renew oxygen level information, and renew melanin information at different time spots), and the processor 22 can generate the user's renew hydration time-variation information, renew oxygen level time-variation information and renew skin oil level time-variation information (please refer to the step S32, which is similar to the step S36). Besides, in an embodiment, the particular period of time can be hours, days, or weeks; while the invention is not limited thereto. In addition, the renew hydration time-variation information, the renew oxygen level time-variation information and the renew skin oil level time-variation information can be defined as the parameters of the user's current skin condition.

Figure 3E:
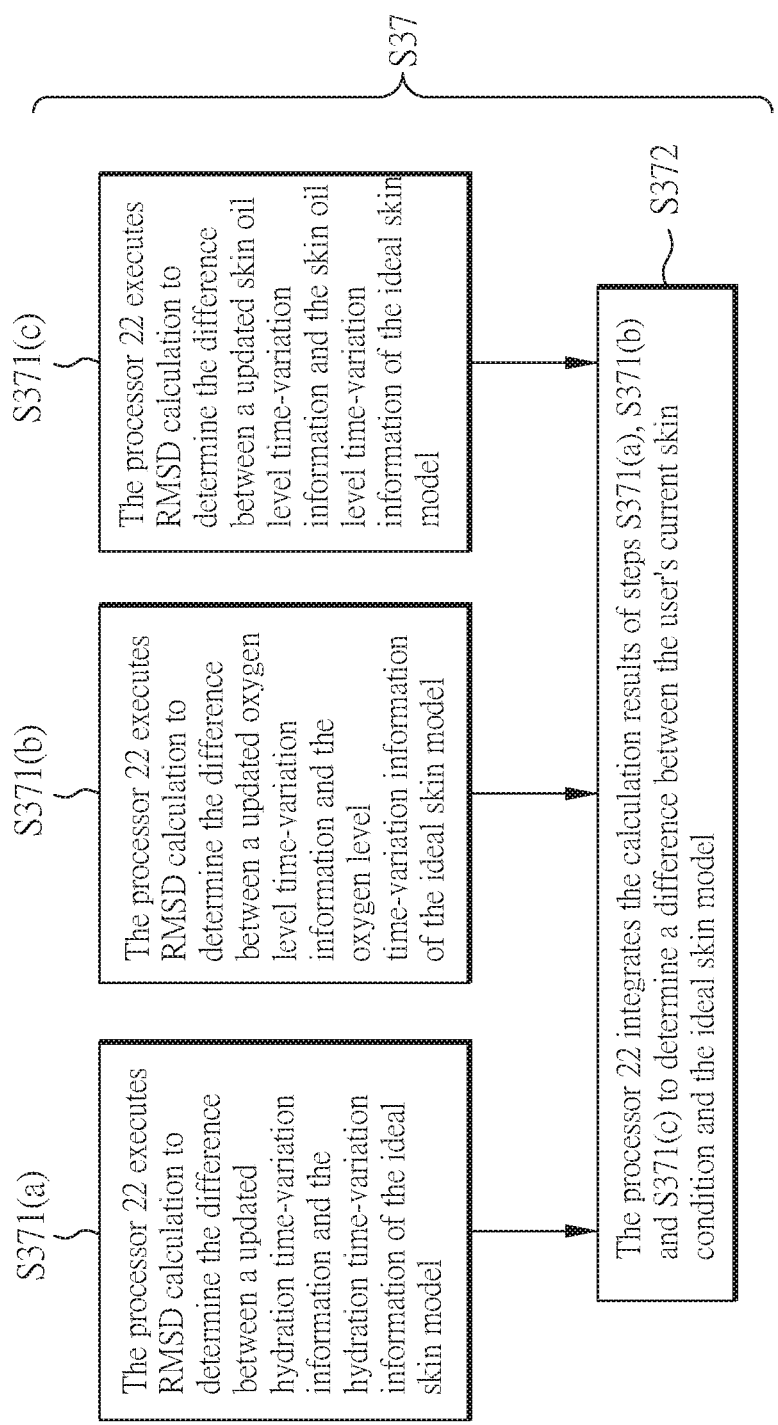

The detail of the step S37 will be described herein. Please refer to FIG. 3(A) and FIG. 3(E), the FIG. 3(E) is a flow chart illustrating the detail of the step S37 in FIG. 3(A).

Wherein, step S371(a) is executed in which, the processor 22 executes RMSD calculation to determine the difference between the renew hydration time-variation information and the predetermined hydration time-variation information of the ideal skin model. Besides, step S371(b) is executed in which, the processor 22 executes RMSD calculation to determine the difference between the renew oxygen level time-variation information and the predetermined oxygen level time-variation information of the ideal skin model. Besides, step S371(c) is executed in which, the processor 22 executes RMSD calculation to determine the difference between the renew skin oil level time-variation information and the predetermined skin oil level time-variation information of the ideal skin model. Then, step S372 is executed in which, the processor 22 integrates the calculation results of the steps S371(a), S371(b) and S371(c) to determine the difference between the user's current skin and the ideal skin model.

The detail of RMSD calculation is described in the aforementioned embodiments, so the detailed description therefor is deemed unnecessary.

Besides, because the skin condition changes slowly, a threshold condition can be inserted to the aforementioned RMSD calculation in order to ensure the availability of the measured information, and thus the availability of the measured information can be determined. Wherein, the threshold condition can be presented by the following function:

$$|Day(n)-Day(n-1)|<5,$$

wherein, Day(n) is the measured results of day n, Day(n−1) is the measured results of day n−1.

The detail of the step S38a will be described herein. In an embodiment, if the processor 22 determines the difference between the user's current skin condition and the ideal skin model is within the first threshold, e.g. the difference is less than or greater to 5% (i.e. |the difference|≤5%), it indicates that the user's current skin condition is similar to the ideal skin model, and thus the personalization suggestion message 26 is effective. Thus, the step S34 is executed again in which, the processor 22 provides the same personalization suggestion message 26.

Then, the detail of the step S38b will be described. In an embodiment, if the processor 22 determines the difference between the user's current skin condition and the ideal skin model is within the second threshold, e.g. the difference is greater than 5% but less than or equal to 30% (i.e. 5%<|the difference|≤30%), it indicates that the user's current skin condition is still different from the ideal skin model, and thus the personalization suggestion message 26 needs to be modified. Therefore, the step S33 is executed again in which, the processor 22 provides a new personalization suggestion message 26. In an embodiment, the modification of the personalization suggestion message 26 can be implemented by adjusting the calculation (please refer to the steps S331 to S333) of the user's skin value, e.g. by adjusting the predetermined weights (a, b, c, d, e, f); while the invention is not limited thereto. Thus, when the personalization skin care product system 1 is continuously executed, the personalization suggestion message 26 can be more suitable for the user.

Then, the detail of the step S38c will be described. In an embodiment, if the processor 22 determines the difference between the user's current skin condition and the ideal skin model is neither within the first threshold nor the second threshold, e.g. the difference is greater than 30% (i.e. 30%<|the difference|), it indicates the user's standard skin model may not be suitable, and thus the user's standard skin model needs to be modified. Therefore, the step S32 is executed again in which, the processor 22 provides a new standard skin model. In an embodiment, the modification of the standard skin model can be implemented by adjusting the RMSD calculation corresponding to the skin model (please refer to the step S321 to S324), e.g. by adjusting the predetermined weights ($a_1$, $a_2$, $a_3$), total number of time (n), etc.; while the invention is not limited thereto. Thus, when the personalization skin care product system 1 is continuously executed, the standard skin model will be more like the user's real skin condition.

The personalization skin care product system 1 can be executed by other operation mechanism. FIG. 4(A) is a flow chart illustrating a method of "providing a personalization suggestion message 26" according to another embodiment of the invention.

First, step S41 is executed in which, the measure device 10 measures a skin information of a user's skin in current time (defined as a first skin information) and/or receives an environment information of the user's current location (defined as a first environment information). Then, step S42 is executed in which, the processor 22 executes the computer program product 24 to calculate a user's skin value (defined as a first skin index) according to the first skin information and/or the first environment information, and then to provide a personalization suggestion message 26 according to the first skin index. Then, step S43 is executed in which, the display screen 28 shows the personalization suggestion message 26.

About the step S41, the first skin information can comprise a hydration information and/or an oxygen level information measured in current time. The first environment information can comprise a temperature information and/or a current humidity of the user's location.

Then, the detail of the step S42 will be described. FIG. 4(B) is a flow chart illustrating the detail of the step S42 according to first example. FIG. 4(C) is a flow chart illustrating the detail of the step S42 according to second example.

First Example

In the first example, the personalization skin care product 50 is a moisturizing skin care product, and the adjustable skin care product device 30 comprises two sub skin care products, wherein one is a serum S1, another is a lotion C1. The ingredients of the serum S1 comprise Hyaluronic acid, Honey, Squalene, Rose water, Agave Leaves Extract, *Camellia Japonica* Extract, Seaweed Extract, Snail Secretion Extract, and Betaine. The ingredients of the lotion C1 comprise Olive Oil, Sweet Almond Oil, Jojoba Oil, Sunflower Oil, Xylitol, Vitamin E, and Poria *Cocos* Extract.

Besides, the data base 40 stores six suggestion messages (defined as output 1 to output 6), and each suggestion message corresponds one skin condition. In addition, the user controllable interface 32 of the adjustable skin care product device 30 has six instructions, and each instruction corresponds to one suggestion message. The adjustable skin care product device 30 can output different volume proportion of the serum S1 and the lotion C1 according to different instruction.

[The Operation of the First Example]

First, step S421 is executed in which, the processor 22 receives the first skin information and the first environment information, wherein the first skin information is a hydration information (defined as X1) of the user's skin measured in current time, and the first environment information is a temperature information (defined as Y1) and a humidity information (defined as Z1) of the user's location.

Then, step S422 is executed in which, the processor 22 calculates the skin index (defined as a first skin index) according to the hydration information X1, the temperature information Y1 and the humidity information Z1, wherein the first skin index can be presented in the following function:

first skin index=$0.5(X1)+0.15(Y1)+0.35(Z1)$;

wherein, the value of the hydration information X1 may be in a range from 0 to 100, the unit of the temperature information Y1 is Celsius, and the unit of the humidity information Z1 is % (Relative humidity, RH).

[The Skin Conditions and the Suggestion Messages in the First Example]

When the first skin index is calculated, step S423 is executed, the processor 22 provides a suggestion message of the six suggestion messages (output1 to output 6) according to a skin condition which the first skin index matched with, it is noted that, the provided suggestion message is provided to the user as the personalization suggestion message 26.

[The skin conditions and the suggestion messages in the first example] When the first skin index is greater than 7, the processor 22 provides a suggestion message (output 1), wherein the suggestion message (output 1) is a suggestion of "outputting 100% lotion C1 and 0% serum S1".

When the first skin index is smaller than or equal to 7, and is greater than 6 (i.e. 6<the first skin index≤7), the processor 22 provides a suggestion message (output 2), wherein the suggestion message (output 2) is a suggestion of "outputting 80% lotion C1 and 20% serum S1".

When the first skin index is smaller than or equal to 6, and is greater than 5 (i.e. 5<the first skin index≤6), the processor 22 provides a suggestion message (output 3), wherein the suggestion message (output 3) is a suggestion of "outputting 60% lotion C1 and 40% serum S1".

When the first skin index is smaller than or equal to 5, and is greater than 4 (i.e. 4<the first skin index≤5), the processor 22 provides a suggestion message (output 4), wherein the suggestion message (output 4) is a suggestion of "outputting 40% lotion C1 and 60% serum S1".

When the first skin index is smaller than or equal to 4, is greater than 2 (i.e. 2<the first skin index≤4), the processor 22 provides a suggestion message (output 5), wherein the suggestion message (output 5) is a suggestion of "outputting 20% lotion C1 and 80% serum S1".

When the first skin index is smaller than or equal to 2 (i.e. the first skin index≤2), the processor 22 provides a suggestion message (output 6), wherein the suggestion message (output 6) is a suggestion of "outputting 0% lotion C1 and 100% serum S1".

Thus, the processor 22 can provide different suggestion message according the user' skin.

Second Example in the first example, the personalization skin care product 50 is a face wash, and the adjustable skin care product device 30 comprises two sub skin care products, wherein one is a gentle face wash S2, another is an oil clear face wash C2. The ingredients of the gentle face wash S2 comprise Water, Sodium Lauroyl Glutamate, Glycerin, Propylene Glycol, Allantion, Sorbitan monooleate, and Hydroxy ethyl cellulose. The ingredients of the oil clear face wash C2 comprise Laurie Acid, Palmitic Acid, Myristic acid, Stearic Acid, Potassium Hydroxide, and Salicylic Acid.

Besides, the data base 40 stores six suggestion messages (defined as output 1 to output 6), and each suggestion message corresponds one skin condition. In addition, the user controllable interface 32 of the adjustable skin care product device 30 has six instructions, and each instruction corresponds to one suggestion message. The adjustable skin care product device 30 can output different volume proportion of the gentle face wash S2 and the oil clear face wash C2 according to different instruction.

[The Operation of the Second Example]

First, step S421' is executed in which, the processor 22 receives the first skin information and the first environment information, wherein the first skin information is a hydration information (defined as X1) and a skin oil level (defined as X2) of the user's skin measured in current time.

Then, step S422' is executed in which, the processor 22 calculates the skin index (defined as a second skin index) according to the hydration information X1 and the skin oil level X2, wherein the second skin index can be presented in the following function:

second skin index=$0.5(X1)+0.5(Y1)$;

wherein, the value of the hydration information X1 may be in a range from 0 to 100, and the value of the skin oil level X2 may be in a range from 0 to 100.

When the second skin index is calculated, step S423' is executed, the processor 22 provides a suggestion message of the six suggestion messages (output1 to output 6) according to a skin condition which the second skin index matched with. It is noted that, the provided suggestion message is provided to the user as the personalization suggestion message 26.

[The Skin Conditions and the Suggestion Messages in the Second Example]

When the second skin index is greater than 7, the processor 22 provides a suggestion message (output 1), wherein the suggestion message (output 1) is a suggestion of "outputting 100% oil clear face wash C2 and 0% gentle face wash S2".

When the second skin index is smaller than or equal to 7, and is greater than 6 (i.e. 6<the second skin index≤7), the processor 22 provides a suggestion message (output 2), wherein the suggestion message (output 2) is a suggestion of "outputting 80% oil clear face wash C2 and 20% gentle face wash S2".

When the second skin index is smaller than or equal to 6, and is greater than 5 (i.e. 5<the second skin index≤6), the processor 22 provides a suggestion message (output 3), wherein the suggestion message (output 3) is a suggestion of "outputting 60% oil clear face wash C2 and 40% gentle face wash S2".

When the second skin index is smaller than or equal to 5, and is greater than 4 (i.e. 4<the second skin index≤5), the processor 22 provides a suggestion message (output 4), wherein the suggestion message (output 4) is a suggestion of "outputting 40% oil clear face wash C2 and 60% gentle face wash S2".

When the second skin index is smaller than or equal to 4, and is greater than 2 (i.e. 2<the second skin index≤4), the processor 22 provides a suggestion message (output 5), wherein the suggestion message (output 5) is a suggestion of "outputting 20% oil clear face wash C2 and 80% gentle face wash S2".

When the second skin index is smaller than or equal to 2 (i.e. the second skin index≤2), the processor 22 provides a suggestion message (output 6), wherein the suggestion message (output 6) is a suggestion of "outputting 0% oil clear face wash C2 and 100% gentle face wash S2".

Thus, the processor 22 can provide different suggestion message according the user' skin.

In conclusion, the personalization skin care product system of the invention can determine the user's standard skin model according to the user's skin information measured at different time spots, and can provide the suitable personalization suggestion message to the user according to the user's skin information, the environment information and the standard skin model. Accordingly, the adjustable skin care product device can provide the suitable personalization skin care product to the user based on the personalization suggestion message. After the user continues to use the personalization suggestion message for a period of time, the personalization skin care product system can determine the effect of the personalization skin care product, and thus can adjust the personalization suggestion message according the effect of the personalization skin care product. Thus, the aforementioned problems relating to the conventional skin care products can be solved.

Although the present invention has been explained in relation to its preferred embodiments, it is to be understood that many other possible modifications and variations can be made without departing from the spirit and scope of the invention as hereinafter claimed.

What is claimed is:

1. A personalization skin care product system (1), comprising:
   a measuring device (10) for measuring a user's skin information; and
   a processor (22) executing a computer program product (24) for providing a personalization suggestion message (26) according to a skin value related to the user's skin information;
   wherein, the personalization suggestion message (26) corresponds to a user controllable interface (32) of an adjustable skin care product device (30), wherein the adjustable skin care product device (30) provides a personalization skin care product (50) with different volume proportion of the ingredients according to the different instructions from the user controllable interface (32);
   wherein the skin value is presented by the following function:

skin value=$a(Td+Hd)+b(Tt+Ht)+cM+dM(t)+eO+fO(t)$, wherein skin value is the user's skin value, Td is an indoor temperature information, Hd is an indoor humidity information, Tt is an outdoor temperature information, Ht is an outdoor humidity information, M is a latest measured hydration information of the user's skin information, M(t) is a predetermined hydration time-variation information of a standard skin model, O is a latest measured oxygen level information of the user's skin information, O(t) is a predetermined oxygen level time-variation information of the standard skin model, a, b, c, d, e, f are predetermined weights corresponding to (Td+Hd), (Tt+Ht), M, M(t), O, O(t).

2. The personalization skin care product system (1) of claim 1, wherein the processor (22) is for providing the standard skin model according to a day-night skin variation information formed by the user's skin information, wherein the day-night skin variation information comprises a hydration time-variation information, an oxygen level time-variation information and a skin oil level time-variation information.

3. The personalization skin care product system (1) of claim 2, wherein the measuring device (10) is for acquiring an environment information, wherein the environment information comprises the indoor temperature information, the indoor humidity information, the outdoor temperature information and the outdoor humidity information.

4. The personalization skin care product system (1) of claim 1, further comprising: a database (40) storing a plurality of skin models and an ideal skin model, wherein each skin model and the ideal skin model corresponds to a predetermined day-night time-variation information, respectively.

5. The personalization skin care product system (1) of claim 4, wherein the processor (22) is for searching a similar skin model stored in the database (40) according to the day-night variation information and the predetermined day-night variation information, and then sets the similar skin model as the standard skin model.

6. The personalization skin care product system (1) of claim 5, wherein the processor (22) determines a difference between a user's current skin information and the ideal skin model after the personalization skin care product (50) is provided, wherein the processer (22) provides the personalization suggestion message (26) again when the difference is within a first threshold range, the processer (22) modifies the personalization suggestion message (26) when the difference is within a second threshold range, wherein the second threshold range does not overlap the first threshold range and the processer (22) modifies the standard skin model when the difference is neither in the first threshold range nor the second threshold range.

7. The personalization skin care product system (1) of claim 1, wherein the measuring device (10) is for acquiring a temperature information and a humidity information, and the skin information comprises a hydration information, and the processer (22) calculates a first skin index according to the hydration information, the temperature information and the humidity information, and provides the personalization suggestion message (26) according to the first skin index, wherein the first skin index is presented in the following function:

the first skin index=$0.5(X1)+0.15(Y1)+0.35(Z1)$;

wherein X1 is the hydration information, Y1 is the temperature information and Z1 is the humidity information.

8. The personalization skin care product system (1) of claim 7, wherein a value of X1 is in a range from 0 to 100, an unit of Y1 is Celsius, and an unit of Z1 is percentage relative humidity.

9. The personalization skin care product system (1) of claim 1, wherein the skin information comprises a hydration information and a skin oil information, and the processer (22) calculates a second skin index according to the hydration information and the skin oil level information, and provides the personalization suggestion message (26) according to the second skin index, wherein the second skin index is presented in the following function:

the second skin index=$0.5(X1)+0.5(X2)$;

wherein X1 is the hydration information, X2 is the skin oil level information.

10. A computer program product (24) for a personalization skin care product system (1), the computer program product (24) executed by a processor (22) and comprising at least a program code for providing:
- an instruction, enabling the processor (22) to receive a user's skin information measured by a measuring device (10);
- an instruction, enabling the processor (22) to provide a personalization suggestion message (26) according to a skin value related to the user's skin information;
- wherein, the personalization suggestion message (26) corresponds to a user controllable interface (32) of an adjustable skin care product device (30), wherein the adjustable skin care product device (30) provides a personalization skin care product (50) with different volume proportion of the ingredients according to the different instructions from the user controllable interface (32);
- wherein, the skin value is presented by the following function:

$$\text{skin value} = a(Td+Hd) + b(Tt+Ht) + cM + dM(t) + eO + fO(t),$$

wherein skin value is the user's skin value, Td is an indoor temperature information, Hd is an indoor humidity information, Tt is an outdoor temperature information, Ht is an outdoor humidity information, M is a latest measured hydration information of the user's skin information, M(t) is a predetermined hydration time-variation information of a standard skin model, O is a latest measured oxygen level information of the user's skin information, O(t) is a predetermined oxygen level time-variation information of the standard skin model, a, b, c, d, e, f are predetermined weights corresponding to (Td+Hd), (Tt+Ht), M, M(t), O, O(t).

11. The computer program product (24) of claim 10, wherein the processor (22) provides the standard skin model according to a day-night skin variation information formed by the user's skin information, wherein the day-night skin variation information comprises a hydration time-variation information, an oxygen level time-variation information and a skin oil level time-variation information.

12. The computer program product (24) of claim 11, wherein the processor (22) receives an environment information acquired by the measuring device (10), wherein the environment information comprises the indoor temperature information, the indoor humidity information, the outdoor temperature information and the outdoor humidity information.

13. The computer program product (24) of claim 11, wherein the at least program code further provides:
- an instruction, enabling the processor (22) to connect to a database (40) storing a plurality of skin models and an ideal skin model, wherein each skin model and the ideal skin model corresponds to a predetermined day-night time-variation information, respectively.

14. The computer program product (24) of claim 13, wherein the at least program code further provides:
- an instruction, enabling the processor (22) to search a similar skin model (42) stored in the database (40) according to the day-night variation information and the predetermined day-night variation information, and to set the similar skin model as the standard skin model.

15. The computer program product (24) of claim 14, wherein the at least program code further provides:
- an instruction, enabling the processor (22) to determine a difference between a user's current skin information and the ideal skin model after the personalization skin care product (50) is provided,
- wherein the processer (22) provides the personalization suggestion message (26) again when the difference is within a first threshold range, the processor (22) modifies the personalization suggestion message (26) when the difference is within a second threshold range, wherein the second threshold range does not overlap the first threshold range and the processer (22) modifies the standard skin model when the difference is neither in the first threshold range nor the second threshold range.

16. The computer program product (24) of claim 11, wherein the at least program code further provides:
- an instruction, enabling the measuring device (10) to acquiring a temperature information and a humidity information, and a hydration information; and
- an instruction, enabling the processer (22) to calculate a first skin index according to the hydration information, the temperature information and the humidity information, and to provide the personalization suggestion message (26) according to the first skin index, wherein the first skin index is presented in the following function:

$$\text{the first skin index} = 0.5(X1) + 0.15(Y1) + 0.35(Z1);$$

wherein X1 is the hydration information, Y1 is the temperature information and Z1 is the humidity information.

17. The computer program product (24) of claim 11, wherein the program code further provides:
- an instruction, enabling the measuring device (10) to acquiring a hydration information and a skin oil level information; and
- an instruction, enabling the processer (22) to calculate a second skin index according to the hydration information and the skin oil level information, and to provide the personalization suggestion message (26) according to the second skin index, wherein the second skin index is presented in the following function:

$$\text{the second skin index} = 0.5(X1) + 0.5(X2);$$

wherein X1 is the hydration information, X2 is the skin oil level information.

18. A personalization skin care product generating method executed by a personalization skin care product system (1), the method comprising the steps of:
- measuring a user's skin information by a measuring device (10); and
- providing a personalization suggestion message (26) according to a skin value related to the user's skin information by a processor (22) executing a computer program product (24);
- wherein, the personalization suggestion message (26) corresponds to a user controllable interface (32) of an adjustable skin care product device (30), wherein the adjustable skin care product device (30) provides a personalization skin care product (50) with different volume proportion of the ingredients according to the different instructions from the user controllable interface (32);
- wherein, the skin value is presented by the following function:

$$\text{skin value} = a(Td+Hd) + b(Tt+Ht) + cM + dM(t) + eO + fO(t),$$

wherein skin value is the user's skin value, Td is an indoor temperature information, Hd is an indoor humidity information, Tt is an outdoor temperature information, Ht is an outdoor humidity information, M is a latest measured hydration information of the user's skin information, M(t) is a predetermined hydration time-variation information of a standard skin model, O is a latest measured oxygen level information of the user's skin information, O(t) is a predetermined oxygen level time-variation information of the standard skin model, a, b, c, d, e, f are predetermined weights corresponding to (Td+Hd), (Tt+Ht), M, M(t), O, O(t).

* * * * *